US012343467B2

(12) United States Patent
Roxhed et al.

(10) Patent No.: US 12,343,467 B2
(45) Date of Patent: Jul. 1, 2025

(54) SPRAY NOZZLE CHIP AND A MEDICAMENT DELIVERY DEVICE COMPRISING THE SAME

(71) Applicant: SHL MEDICAL AG, Zug (CH)

(72) Inventors: Niclas Roxhed, Bromma (SE); Torben Last, Osterode am Harz (DE); Göran Stemme, Lidingö (SE)

(73) Assignee: SHL Medical AG, Zug (CH)

( * ) Notice: Subject to any disclaimer, the term of this patent is extended or adjusted under 35 U.S.C. 154(b) by 708 days.

(21) Appl. No.: 17/418,380

(22) PCT Filed: Dec. 27, 2019

(86) PCT No.: PCT/EP2019/087074

§ 371 (c)(1),
(2) Date: Jun. 25, 2021

(87) PCT Pub. No.: WO2020/151897

PCT Pub. Date: Jul. 30, 2020

(65) Prior Publication Data

US 2022/0072241 A1 Mar. 10, 2022

(30) Foreign Application Priority Data

Jan. 25, 2019 (EP) .................................... 19153766

(51) Int. Cl.
*A61M 11/00* (2006.01)
*A61F 9/00* (2006.01)
*B05B 11/00* (2023.01)
*B05B 15/40* (2018.01)

(52) U.S. Cl.
CPC ......... *A61M 11/003* (2014.02); *A61F 9/0008* (2013.01); *B05B 11/007* (2013.01);
(Continued)

(58) Field of Classification Search
CPC ......... B05B 1/14; B05B 15/40; B05B 11/007; A61M 11/006; A61M 11/007;
(Continued)

(56) References Cited

U.S. PATENT DOCUMENTS

2007/0179428 A1* 8/2007 Kralick ............... F16K 99/0028 604/9
2007/0275193 A1* 11/2007 DeSimone ........ B01L 3/502738 427/532
(Continued)

FOREIGN PATENT DOCUMENTS

WO WO-0218058 A1 * 3/2002 .............. A01J 11/06
WO WO-2016203225 A1 * 12/2016 ........... A61F 9/0008
WO WO-2017095220 A1 * 6/2017 ............... B05B 1/14

OTHER PUBLICATIONS

"Parylene Vapor Deposited Conformal Coating—Basics" Parylene Engineering, Aug. 24, 2018. https://www.paryleneengineering.com/parylene_basic.htm (Year: 2018).*
(Continued)

*Primary Examiner* — Victoria Murphy
*Assistant Examiner* — Sara K Toich
(74) *Attorney, Agent, or Firm* — McDonnell Boehnen Hulbert & Berghoff LLP

(57) ABSTRACT

A spray nozzle chip comprising: a first layer provided with a first layer orifice, and a mechanically flexible nozzle layer provided with a nozzle orifice, wherein the first layer has a valve seat arranged aligned with the nozzle orifice, wherein the spray nozzle chip has a valve functionality obtained by movement of the nozzle layer relative to the valve seat due to pressure changes, and wherein the nozzle layer is arranged at a distance from the valve seat when the nozzle layer is in a default non-pressurised state, whereby a gap with a gap length (L) is formed between the nozzle layer and the valve seat, wherein the gap length (L) is smaller than a
(Continued)

dimension of a specific bacterial type, to thereby seal against bacterial ingrowth through the nozzle orifice of the specific bacterial type.

9 Claims, 5 Drawing Sheets

(52) U.S. Cl.
CPC .......... *B05B 11/0072* (2013.01); *B05B 15/40* (2018.02); *A61M 2207/00* (2013.01)

(58) Field of Classification Search
CPC ....... A61M 15/00; A61M 11/003; F16K 7/17; F16K 99/0001; F16K 99/0015; F16K 99/0026; B01D 67/0088; B01D 67/0093
See application file for complete search history.

(56) References Cited

U.S. PATENT DOCUMENTS

2011/0132480 A1* 6/2011 Chappel ................ A61M 37/00 137/599.06
2013/0211313 A1* 8/2013 Dos Santos ......... A61F 9/00781 604/9
2016/0175863 A1 6/2016 Bloc

OTHER PUBLICATIONS

International Search Report and Written Opinion for Int. App. No. PCT/EP2019/087074, mailed Apr. 1, 2020.

* cited by examiner

SPRAY NOZZLE CHIP AND A MEDICAMENT DELIVERY DEVICE COMPRISING THE SAME

CROSS REFERENCE TO RELATED APPLICATIONS

The present application is a U.S. National Phase Application pursuant to 35 U.S.C. § 371 of International Application No. PCT/EP2019/087074 filed Dec. 27, 2019, which claims priority to European Patent Application No. 19153766.1 filed Jan. 25, 2019. The entire disclosure contents of these applications are herewith incorporated by reference into the present application.

TECHNICAL FIELD

The present disclosure generally relates to a spray nozzle chip and to a medicament delivery device comprising a spray nozzle chip.

BACKGROUND

A nozzle device may be configured to atomise a fluid, i.e. to make an aerosol of the fluid. A nozzle device of this type may comprise a sieve membrane provided for filtering out any undesired larger particles contained in the fluid to be atomised. The nozzle device may also include a nozzle membrane with one or more orifices. The nozzle membrane and the sieve membrane are configured to be in fluid communication. In the process of atomisation, the fluid first passes the sieve membrane. The filtered fluid subsequently passes through the one or more orifices of the nozzle membrane, whereby the fluid is atomised.

An example of a nozzle device is disclosed in WO 2016/203225 A1. The nozzle assembly disclosed in WO 2016/203225 A1 is configured to receive fluid at pressures of greater than 1 bar. The nozzle assembly comprises a first perforate element comprising one or more orifices, each orifice having an inlet and an outlet and a diameter of no more than 100 μm, and at least one second perforate element further comprising a plurality of orifices of a smaller size than the one or more orifices of the first perforate element and having a larger number of orifices than the first perforate element. The second perforate element is configured to act as a filter and the second perforate element is attached to the first perforate element. A perpendicular distance between the first and second perforate elements is less than the diameter of the largest orifice of the first perforate element in order to prevent contamination.

Drug solutions for fluidic micro- or nanojet-based medical devices such as inhaler systems for drug delivery are liquid and may be stored in a single drug container inside the inhaler system. Multiple treatments may be administered from the inhaler system from the liquid drug container. For these types of devices bacterial ingrowth through the spray nozzle poses a severe problem, as such ingrowth into the liquid drug container can render the device unsafe for medical treatment.

SUMMARY

Bacterial contamination can arise due to two transport mechanisms: motility and ingrowth. If the channel height of the nozzle membrane allows the bacteria to be motile, contamination may occur on a timescale of seconds, depending on the Rayleigh number inside the channel. Once the channel height is small enough to hinder motile movement of the bacterium it may still pass the channel by ingrowth. This contamination mechanism acts on much larger timescales, but bacteria are able to pass channels smaller than their own dimensions and proliferate afterwards.

In view of the above, a general object of the present disclosure is to provide a spray nozzle chip which solves or at least mitigates problems of the prior art.

There is hence according to a first aspect of the present disclosure provided a spray nozzle chip comprising: a first layer provided with a first layer orifice, and a mechanically flexible nozzle layer provided with a nozzle orifice, wherein the first layer has a valve seat arranged aligned with the nozzle orifice, wherein the spray nozzle chip has a valve functionality obtained by movement of the nozzle layer relative to the valve seat due to pressure changes, and wherein the nozzle layer is arranged at a distance from the valve seat when the nozzle layer is in a default non-pressurised state, whereby a gap with a gap length L is formed between the nozzle layer and the valve seat, wherein the gap length L is smaller than a dimension of a specific bacterial type, to thereby seal against bacterial ingrowth through the nozzle orifice of the specific bacterial type.

Due to the small size of the gap length relative to specific bacterial type, the spray nozzle chip self-seals against bacterial ingrowth of the specific bacterial type. Safe reuse of the spray nozzle chip for multiple spray operations over an extended period of time may thereby be provided.

The dimension of the specific bacterial type may for example be a diameter or a length of the specific bacterial type. The dimension may for example be the smallest dimension of the specific bacterial type or an average dimension e.g. average diameter or length, of a specific bacterial type.

The spray nozzle chip may be configured to be used in a medicament delivery device.

According to one embodiment the first layer and the nozzle layer are connected together by means of an intermediate layer, such as a bonding layer, or a spacer layer, the thickness of which at least partly defines the gap length L.

According to one embodiment the intermediate layer is a metal or a metal alloy, a ceramic or a monolayer According to one embodiment the valve seat is also provided with the intermediate layer thereby forming a valve seat intermediate layer arranged at a distance from the nozzle layer, wherein the thickness of the valve seat intermediate layer relative to a thickness of the intermediate layer, which connects the first layer and the nozzle layer, defines the gap length L.

According to one embodiment the gap length L is at least 30% smaller than the dimension of the specific bacterial type, such as at least 50% smaller than the dimension of the specific bacterial type.

The gap length L may for example be in the range 0.5-1000 nm, or more preferably 0.5-300 nm, such as 0.5 nm$<$gap length L$\leq$300 nm.

In practice, a gap length of approximately 0.5 nm is the smallest possible gap, since the gap length L of two abutting layers is determined by the surface roughness, which is around 0.5 nm for polished silicon wafers.

According to one embodiment the intermediate layer comprises a biocompatible polymer.

According to one embodiment the biocompatible polymer is Parylene, such as Parylene-C.

According to one embodiment the first layer is a sieve layer and the first layer orifice is a sieve orifice.

One embodiment comprises outer walls formed partly by the first layer and the nozzle layer, wherein the valve seat is arranged between the outer walls, wherein the nozzle layer has a width defined by a distance between the outer walls, and wherein the nozzle layer has a length, wherein of the width and the length, the valve functionality is determined only by the width.

According to one embodiment the nozzle layer comprises a plurality of nozzle orifices arranged along the length of the nozzle layer.

According to one embodiment the nozzle orifice is aligned with the valve seat.

One embodiment comprises a conformal coating provided on the first layer and on the nozzle layer. The gap length L may thereby be fine tuned based on the thickness of the conformal coating.

There is according to a second aspect of the present disclosure provided a medicament delivery device comprising the spray nozzle chip according to the first aspect.

The medicament delivery device may for example be an inhaler or an eye dispenser.

There is according to a third aspect of the present disclosure provided a method of manufacturing a spray nozzle chip according to the first aspect, the method comprising: a) providing a first layer which has a first layer orifice, the first layer having a valve seat, b) providing a nozzle layer which has a nozzle orifice, c) providing at least one of the first layer and the nozzle layer with an intermediate layer, and d) connecting the first layer with the nozzle layer by means of the intermediate layer.

According to one embodiment step c) involves providing the first layer with a first intermediate layer and the valve seat with a valve seat intermediate layer, and providing the nozzle layer with a second intermediate layer, wherein step d) involves connection by means of the first intermediate layer and the second intermediate layer.

According to one embodiment the first intermediate layer is thicker than the second intermediate layer.

According to one embodiment the first intermediate layer and the valve seat intermediate layer are provided onto the first layer simultaneously in step c).

The intermediate layer may be a bonding layer, which connects the first layer with the nozzle layer by a bonding technique known in the art, such as fusion bonding, eutectic bonding or thermocompression bonding. The bonding layer may alternatively be an adhesive bonding layer, such as a biocompatible layer or a medical grade material. An example of a biocompatible bonding layer is Parylene, especially Parylene C.

The intermediate layer may alternatively be a spacer layer, which mainly serves to define the gap length L, and whose bonding properties are of minor significance.

There is hence according to a fourth aspect of the present disclosure provided a spray nozzle chip comprising a first layer provided with a first layer orifice, and a mechanically flexible nozzle layer provided with a nozzle orifice, wherein the first layer has a valve seat arranged aligned with the nozzle orifice, wherein the spray nozzle chip has a valve functionality obtained by movement of the nozzle layer relative to the valve seat due to pressure changes, and wherein the nozzle layer is arranged internally strained towards the valve seat and in physical contact with the valve seat when the nozzle layer is in a default non-pressurised state, such that a fluid passage between the nozzle layer and the valve seat is closed to thereby seal against bacterial ingrowth through the nozzle orifice, and wherein the nozzle layer is deflectable to open the fluid passage when the nozzle layer is subjected to a differential pressure.

The internally strained nozzle layer is thus closed in the default non-pressurised state, and open when subjected to the differential pressure. The lowest differential pressure required to open the fluid passage may be approximately between 0.1 bar and 20 bar. The required differential pressure may be adapted by adjusting layer thicknesses and a width w between walls of the spray nozzle chip.

According to one embodiment, the valve seat of the spray nozzle chip may have a valve seat intermediate layer, the thickness of which is greater than the thickness of the intermediate layer, thereby forming a raised surface of the valve seat towards which the nozzle layer is internally strained, and wherein the thickness of the valve seat intermediate layer relative to a thickness of the intermediate layer defines the gap length L.

The valve seat intermediate layer may thus be used to create the raised surface, which determines the gap length, which gap length of this fourth aspect of the disclosure is the physical lower limit of the gap length, e.g. 0.5 nm, as described above.

According to one embodiment the spray nozzle chip the intermediate layer is a bonding layer and the bonding connection between the valve seat intermediate layer and the nozzle layer initially forms a hermetic seal, which seal is breakable by subjecting the nozzle layer to a differential pressure for a first time.

The hermetic seal effectively ensures that the nozzle chip prevents bacterial ingrowth through the nozzle orifice for extended periods of time, such as when a medicament delivery device, with which the nozzle chip is assembled, is stored for a long time before being put into use.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

Some embodiments will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
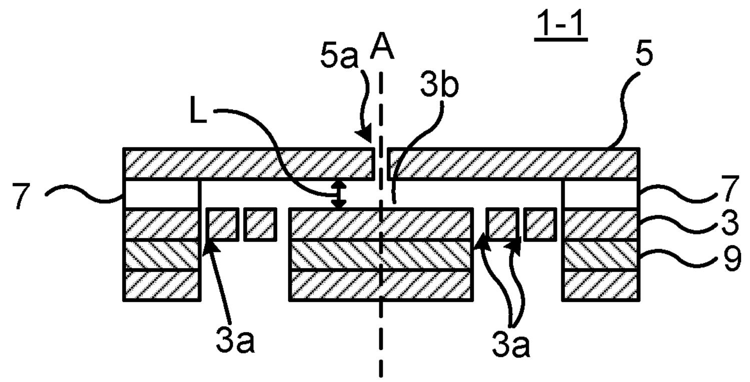
FIG. 1 schematically shows a section of an example of a spray nozzle chip.

FIG. 1 shows an example of a spray nozzle chip 1-1 in a non-pressurised default state. The spray nozzle chip 1-1 may be a microjet spray nozzle chip 1-1. This applies to all of the examples disclosed herein. The spray nozzle chip 1-1 comprises a first layer 3. The first layer 3 may be a sieve layer. The first layer 3 may be a sieve membrane. The first layer 3 is provided with a plurality of first layer orifices 3*a*. The first layer orifices 3*a* may be sieve layer orifices. The first layer 3 has a valve seat 3*b*. In the section through the spray nozzle chip 1-1 shown in FIG. 1, the valve seat 3*b* forms the centre of the first layer 3, although a central alignment is not essential. The spray nozzle chip 1-1 has a spray axis A, along which the main component of the liquid droplets initially propagate when exiting the spray nozzle chip 1-1. According to the example, the first layer orifices 3*a* are provided around the spray axis A. In the exemplary embodiment of FIG. 1, the valve seat 3*b* is centred on the spray axis A.

The spray nozzle chip 1-1 also includes a nozzle layer 5. The nozzle layer 5 is mechanically flexible. The nozzle layer 5 may be a nozzle membrane. The nozzle layer 5 may be arranged parallel or substantially parallel with the first layer 3. The nozzle layer 5 has a nozzle orifice 5*a*. The nozzle orifice 5*a* is aligned with the spray axis A. The spray axis A is thus an axis of the nozzle orifice 5*a*. The nozzle orifice 5*a* is hence arranged aligned with the valve seat 3*b*. The nozzle orifice 5*a* may be centred over the valve seat 3*b*.

The nozzle layer 5 and the first layer 3 are spaced apart. A gap is hence formed between the nozzle layer 5 and the first layer 3. The gap is in particular formed between the nozzle layer 5 and the valve seat 3*b*. The nozzle layer 5 is arranged at a gap length L from the valve seat 3*b*. The inner perimeter of the nozzle orifice 5*a* is hence arranged at the gap length L from the valve seat 3*b*. The gap is present when the spray nozzle chip 1-1 and the nozzle layer 5 are in the default non-pressurised state. The gap length L is smaller than a dimension of a specific bacterial type. The gap length L may for example be at least 20% smaller than the dimension of the specific bacterial type, i.e. the gap length L may be at most 80% of the dimension of the specific bacterial type, such as at least 30% smaller, 40% smaller, 50% smaller, or 60% smaller than the dimension of the specific bacterial type. This applies to any example disclosed herein.

The spray nozzle chip 1-1 has an intermediate layer 7 which connects the first layer 3 with the nozzle layer 5. The gap is in this example formed by the thickness of the intermediate layer 7. The gap length L is hence defined by the thickness of the intermediate layer 7, in particular in its state after connection. The intermediate layer 7 may become compressed once the first layer 3 and the nozzle layer 5 have been connected. The intermediate layer 7 acts as a spacer between the first layer 3 and the nozzle layer 5. In this example, the valve seat 3*b* is not provided with any coating for tuning the gap length L. The gap length L is in this example hence solely defined by the thickness of the intermediate layer 7 when the first layer 3 and the nozzle layer 5 have been connected.

Figure 2:
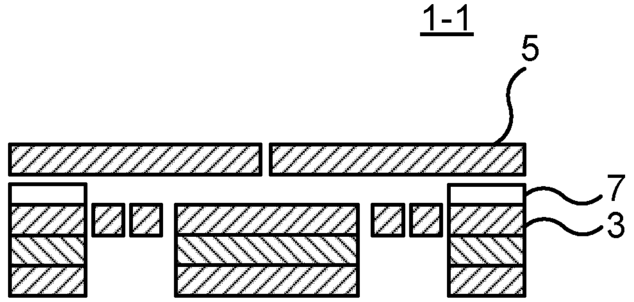
FIG. 2 schematically shows a section of the spray nozzle chip in FIG. 1 before connection, e.g. by bonding.

The intermediate layer 7 may comprise a bonding layer, such as a biocompatible polymer. Such a biocompatible polymer may for example be structured Parylene e.g. Parylene-C, which may act as an adhesive layer. FIG. 2 shows the spray nozzle chip 1-1 before connection, i.e. bonding, of the first layer 3 with the nozzle layer 5. The bonding layer is in this example deposited onto the first layer 3. The valve seat 5*b* is free from the bonding layer before bonding. The nozzle layer 5 and the structure comprising the first layer 3 may then for example be thermocompression bonded by means of the bonding layer.

The first layer 3 and the nozzle layer 5 form part of a substrate structure which may be formed by bonding a plurality of layers. The first layer 3 and the nozzle layer 5 may for example be made of silicon. The first layer 3 and the nozzle layer 5 may for example be fabricated from silicon-on-insulator (SOI) wafers. A layer 9 adjacent to the first layer 3 may for example be made of silicon dioxide. It should be noted that other materials may also be used to form the spray nozzle structure 1-1. The intermediate layer 7 may for instance be a bonding layer of a metal or a metal alloy, a ceramic or a monolayer.

The first layer 3 and the nozzle layer 5 may be bonded by techniques such as fusion bonding, eutectic bonding or thermocompression. The intermediate layer 7 may alternatively be a spacer layer, i.e. a non-bonding layer, which instead of bonding mainly serves as a structure to create the gap L. The first layer 3 and the nozzle layer 5 may then be connected along other mutually interfacing surfaces (not shown).

Figure 3:
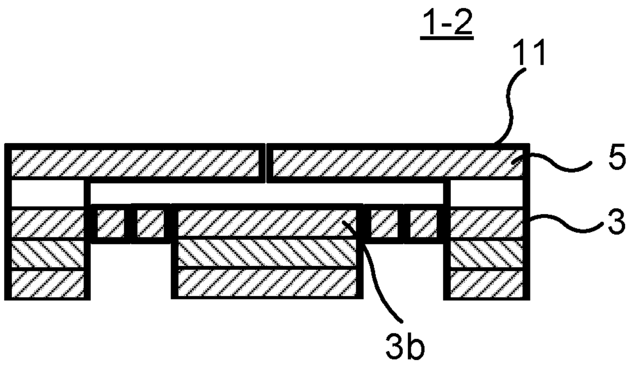
FIG. 3 schematically shows a section of an example of a spray nozzle chip.

FIG. 3 shows an example of a spray nozzle chip 1-2 which is similar to spray nozzle chip 1-1. The spray nozzle chip 1-2 however additionally comprises a conformal coating 11. The conformal coating 11 is provided on and/or around the first layer 3 and on the nozzle layer 5. The conformal coating 11 may for example be implemented using a biocompatible polymer such as Parylene or atomic layer deposition (ALD). The gap length L may thereby be fine-tuned based on the thickness of the conformal coating 11.

Figure 4:
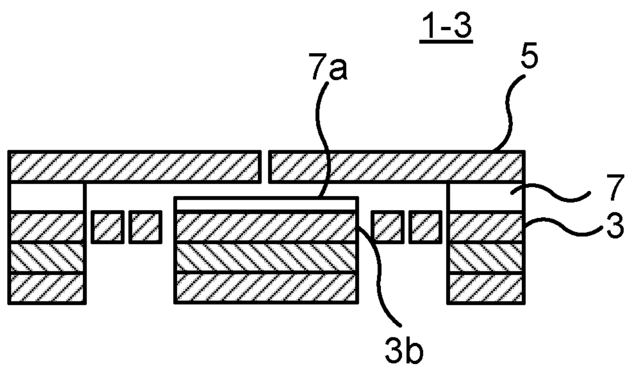
FIG. 4 schematically shows a section of an example of a spray nozzle chip.

FIG. 4 shows another example of a spray nozzle chip. The spray nozzle chip 1-3 is similar to the spray nozzle chip 1-1. In the example depicted in FIG. 4, the valve seat 3*b* is however provided with a valve seat intermediate layer 7*a*. The valve seat intermediate layer 7*a* hence forms part of the valve seat 3*b*. The first layer 3 and the nozzle layer 5 are connected by means of the intermediate layer 7 but not by means of the valve seat intermediate layer 7*a*. The valve seat intermediate layer 7*a* does hence in this sense not have any bonding functionality. In this example, the valve seat intermediate layer 7*a* is thinner than the intermediate layer 7 which connects the first layer 3 and the nozzle layer 5. The gap length L between the valve seat 3*a*, in particular the valve seat intermediate layer 7*a*, and the nozzle layer 5 is in this case defined by the thickness of the intermediate layer 7 relative to the thickness of the valve seat intermediate layer 7*a*. The difference between these two thicknesses when the first layer 3 and the nozzle layer 5 have been connected, e.g. bonded, defines the gap length L.

Figure 5:
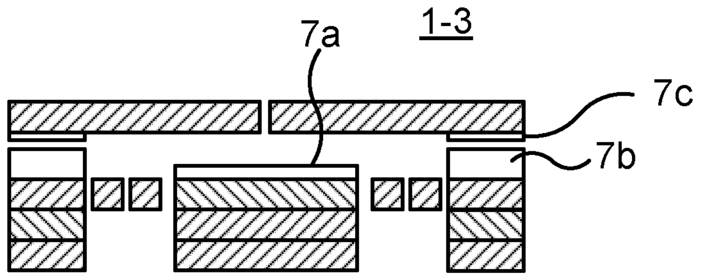
FIG. 5 schematically shows a section of the spray nozzle chip in FIG. 4 before connection, e.g. by bonding.

FIG. 5 shows an example of how the first layer 3 and the nozzle layer 5 may be connected by means of the intermediate layer 7. The intermediate layer acts as an adhesive or as a spacer layer. The intermediate layer 7 may be formed of two layers, namely a first intermediate layer 7*b* which also forms the valve seat intermediate layer 7*a* and which is provided on the first layer 3, and a second intermediate layer 7*c* which is provided on the nozzle layer 5. The first intermediate layer 7*b*, which includes the valve seat intermediate layer 7*a*, may have a uniform thickness. The second intermediate layer 7*c* may have a different thickness than the first intermediate layer 7*b*. The second intermediate layer 7*c* may hence have a different thickness than the valve seat intermediate layer 7*a*. For example, the first intermediate layer 7*b* may be thicker than the second intermediate layer 7*c*. In the case where the intermediate layers are bonding layers, the nozzle layer 5 and the first layer 3 may for example be thermocompression bonded by means of the first intermediate layer 7*b* and the second intermediate layer 7*c*, which thereby form the intermediate layer 7 shown in FIG. 4.

Advantageously, the bond strength of a Parylene bond is higher when deposited on both surfaces to be bonded as in this case both surfaces can be surface modified i.e. using a silane solution which increases Parylene adhesion during the deposition process.

In a variation of the spray nozzle chip 1-3 shown in FIG. 4, the spray nozzle chip may additionally be provided with a conformal coating. The gap length L may thereby be further fine tuned.

Figure 6:
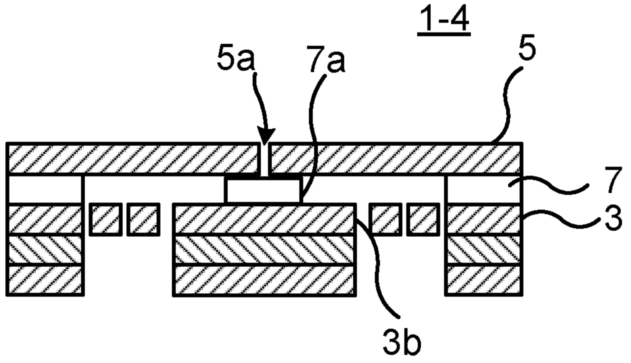
FIG. 6 schematically shows a section of yet another example of a spray nozzle chip.

FIG. 6 shows an example of a spray nozzle chip similar to the example shown in FIG. 4. The spray nozzle chip 1-4 however has a portion of the valve seat 3*b* provided with the valve seat intermediate layer 7*a* with a thickness essentially the same as the gap length L. The valve seat intermediate layer 7*a* may thereby provide a connection, i.e. bonding, between the first layer 3 and the nozzle layer 5. The valve seat intermediate layer 7*a* may hence act as a sealing of the nozzle orifice 5*a* before the spray nozzle chip 1-4 is initially used. When the spray nozzle chip 1-4 is initially used, the sealing provided by the valve seat intermediate layer 7*a* is broken by the differential pressure acting on the first layer 3, thereby opening the nozzle orifice 5*a* and enabling a spray operation.

As a variation to the above, the nozzle layer could also or alternatively be provided with an intermediate layer circumferentially around the nozzle orifice. The thickness of this intermediate layer could be used to define the gap length between the valve seat and the nozzle layer.

Figure 7:
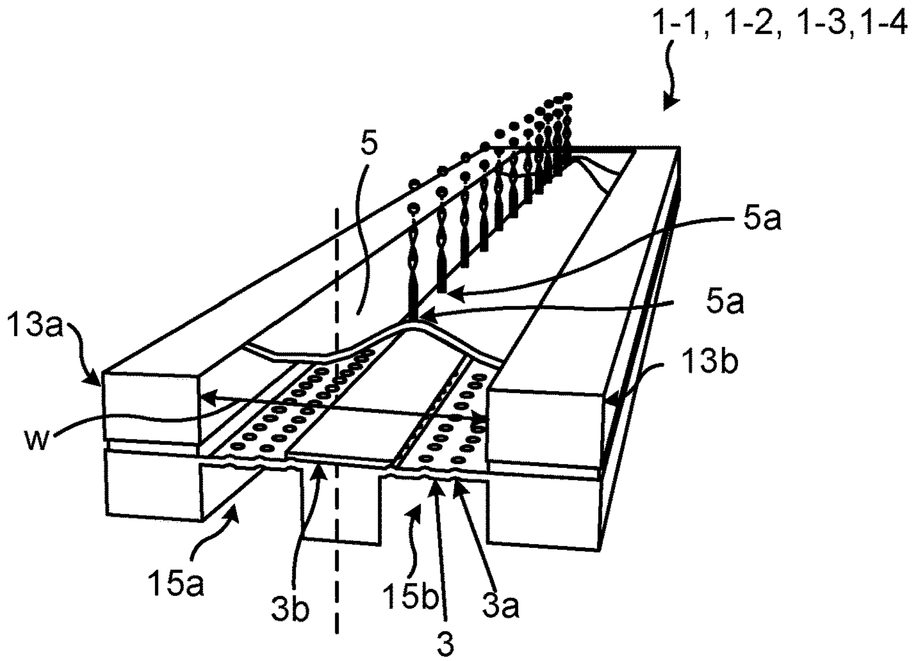
FIG. 7 schematically depicts a perspective view of a cross-section of a spray nozzle chip.

FIG. 7 depicts a section through an example of a spray nozzle chip, seen in a perspective view. The exemplified spray nozzle chip, which may be any one of the spray nozzles 1-1 to 1-4, has a generally rectangular shape. In particular, the nozzle layer 5 and the first layer 3 may have a generally rectangular shape. A plurality of layers, including the first layer 3 and the nozzle layer 5 may be connected, e.g. by bonding, and form parallel long side outer walls 13*a* and 13*b*. The valve seat 3*b* is in the depicted example arranged between and centred with respect to the two facing outer walls 13*a* and 13*b*. The valve seat 3*b* extends longitudinally, generally in parallel, with the two outer walls 13*a* and 13*b*. A first fluid channel 15*a* is provided between one of the outer walls 13*a* and the valve seat 3*b*. The first layer 3 comprises a plurality of first layer orifices 3*a* distributed along the length of the first layer 3, opening into the first fluid channel 15*a*. A second fluid channel 15*b* parallel with the first fluid channel 15*a* is provided between the other one of the outer walls 13*b* and the valve seat 3*b*. The first layer 3 comprises a plurality of first layer orifices 3*a* distributed along the length of the first layer 3, opening into the second fluid channel 15*b*. The first fluid channel 15*a* and the second fluid channel 15*b* may be in fluid communication with a fluid container such as a medicament container.

The nozzle layer 5 comprises a plurality of nozzle orifices 5*a* arranged along the length of the valve seat 3*b*. The nozzle orifices 5*a* may be distributed along the nozzle layer 5 as it extends between the two short sides of the spray nozzle chip 1-1 to 1-4. The nozzle layer 5 has a width w defined by a distance between the long side outer walls 13*a* and 13*b*. The nozzle layer 5 also has a length defined by the distance between the short side outer walls of the spray nozzle chip 1-1 to 1-4. The valve functionality provided by the nozzle layer 5 is determined only by the dimension of the width w. The valve functionality is that provided by the nozzle layer 5 and the valve seat 3*b*. In a non-pressurised state, the nozzle layer 5 is close enough to the valve seat 3*b* that the nozzle orifice 5*a* may be considered to be closed. When the differential pressure acting on the nozzle layer 5 is large enough, the nozzle layer 5 is deflected away from the valve seat 3*b* enabling spraying through the nozzle orifice 5*a*.

The spray nozzle chip 1-1 to 1-4 could alternatively have another shape than being rectangular. The spray nozzle chip 1-1 to 1-4 could for example be circular, elliptical, polygonal, etc.

Figure 8:
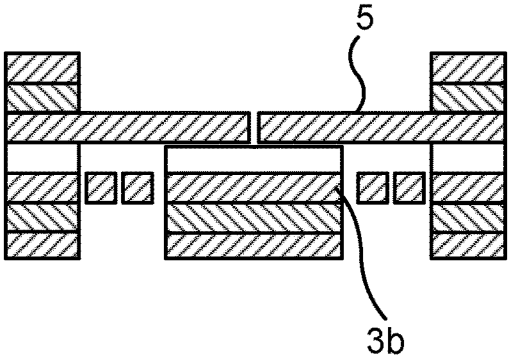
FIG. 8 schematically depicts a section of a spray nozzle chip in a default non-pressurised state.
Figure 9:
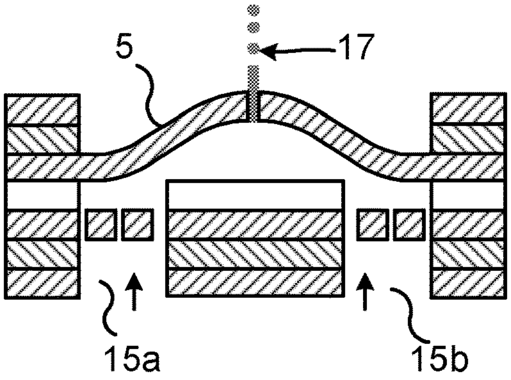
FIG. 9 shows the spray nozzle chip in FIG. 8 in a pressurised state.

FIG. 8 schematically shows a general example of a spray nozzle chip according to any example disclosed herein. The spray nozzle chip in FIG. 8 is shown in a default non-pressurised state. FIG. 9 illustrates a spray operation. The nozzle layer 5 is subjected to a differential pressure of for example more than 20 bar, resulting in that the nozzle layer is deflected away from the first layer 3. The fluid flowing through the first fluid channel 15*a* and the second fluid channel 15*b* from a fluid container passes through the first orifices 3*a* and the nozzle orifices 5*a*, resulting in an aerosol 17. After the spray operation, the nozzle layer 5 returns to the initial state, thereby restoring the microbial barrier with the gap length L.

Figure 10:
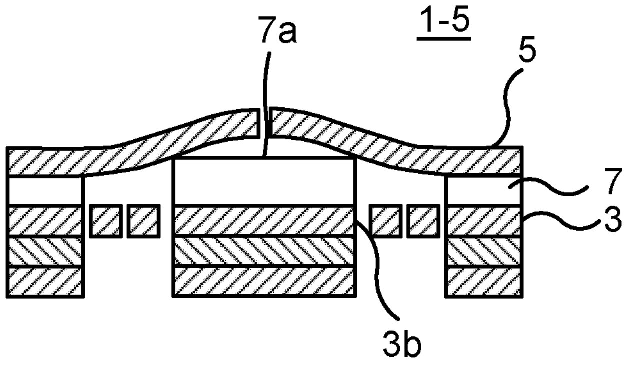
FIG. 10 schematically depicts a section of a spray nozzle chip in a default non-pressurised state.

FIG. 10 shows an alternative example of a spray nozzle chip. The spray nozzle chip 1-5 is similar to the spray nozzle chip 1-3. In the example depicted in FIG. 10, the valve seat 3*b* is however provided with a valve seat intermediate layer 7*a* of a greater thickness than the intermediate layer 7. The valve seat intermediate layer 7*a* hence forms a raised surface relative to the intermediate layer 7. The first layer 3 and the nozzle layer 5 are connected by means of the intermediate layer 7. The first layer 3 and the nozzle layer 5 may also be connected by means of the valve seat intermediate layer 7*a*. The valve seat intermediate layer 7*a* may hence in this sense have a bonding functionality. If the valve seat intermediate layer 7*a* has a bonding functionality, the bond of the valve seat intermediate layer is configured to rupture when a liquid product is pressurised for a first delivery of an aerosol, i.e. when the nozzle layer 5 is subjected to differential pressure for the first time. In this example, the valve seat intermediate layer 7*a* is thicker than the intermediate layer 7 which connects the first layer 3 and the nozzle layer 5. There is thus defined a gap length L between the valve seat 3*b*, in particular the valve seat intermediate layer 7*a*, and the nozzle layer 5 as measured in an area where the nozzle layer 5 is connected to the intermediate layer 7. The gap L is in this case defined by the thickness of the intermediate layer 7 relative to the thickness of the valve seat intermediate layer 7*a*. The difference between these two thicknesses when the first layer 3 and the nozzle layer 5 have been connected, e.g. bonded, defines the gap length L.

In practice, the raised valve seat intermediate layer 7*a* and the gap L result in the nozzle layer 5, in the default non-pressurised state, being in physical contact with the valve seat intermediate layer 7*a*, and arched over the valve seat intermediate layer 7*a*. As previously described, this results in a gap length L of at least 0.5 nm, depending on the surface roughness of the nozzle layer 5 and the valve seat intermediate layer 7*a*. The nozzle layer 5, is thus strained against the valve seat intermediate layer 7*a*, thereby forming an anti-bacterial barrier at an interface between the strained nozzle layer 5 and the valve seat intermediate layer 7*a*. The interface may be defined as a fluid passage 21 which may be closed or opened as a function of the differential pressure applied to the nozzle layer 5. When the fluid passage 21 is closed, the gap length depends on the surface roughness of the abutting layers. It is envisaged that the gap length L is at least approximately 0.5 nm.

Figure 11:
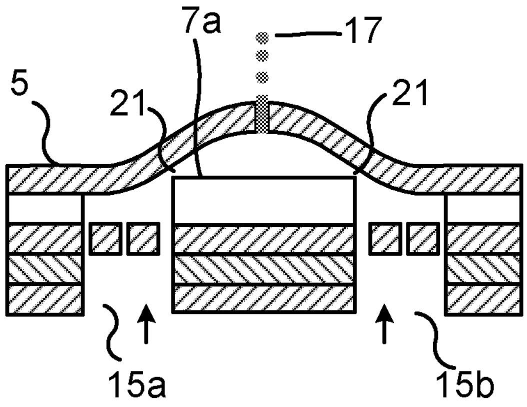
FIG. 11 shows the spray nozzle chip in FIG. 10 in a pressurised state.

FIG. 11 illustrates a spray operation of the nozzle chip 1-5, corresponding to the spray operation shown in FIG. 9. The nozzle layer 5 is subjected to a differential pressure of for example more than 20 bar, resulting in that the nozzle layer 5 is deflected away from the first layer 3 and the valve seat intermediate layer 7*a*. The fluid flowing through the first fluid channel 15*a* and the second fluid channel 15*b* from a fluid container passes through the first orifices 3*a*, via the fluid passage 21 between the nozzle layer 5 and the valve seat intermediate layer 7*a*, and through the nozzle orifices 5*a*, resulting in an aerosol 17. The fluid passage 21 between the nozzle layer 5 and the valve seat intermediate layer 7*a* is opened by the differential pressure. After the spray operation, the nozzle layer 5 returns to the initial state, thereby closing the fluid passage 21 and restoring the microbial barrier with the gap length L.

The first application of the differential pressure may break a bond between the nozzle layer 5 and the valve seat intermediate layer 7*a*, in the case where the valve seat intermediate layer 7*a* is a bonding layer. Prior to breaking and rupturing the bond, the bond serves as a hermetic and anti-microbial seal against bacterial ingrowth through the nozzle orifice 5*a*.

In accordance with this alternative embodiment, there is provided a spray nozzle chip 1-5 comprising a first layer 3 provided with a first layer orifice 3*a*, and a mechanically flexible nozzle layer 5 provided with a nozzle orifice 5*a*, wherein the first layer 3 has a valve seat 3*b* arranged aligned with the nozzle orifice 5*a*, wherein the spray nozzle chip 1-5 has a valve functionality obtained by movement of the nozzle layer 5 relative to the valve seat 3*b* due to pressure changes, and wherein the nozzle layer 5 is arranged internally strained towards the valve seat 3*b* and in physical contact with the valve seat 3*b* when the nozzle layer 5 is in a default non-pressurised state, such that a fluid passage 21 between the nozzle layer 5 and the valve seat 3*b* is closed to thereby seal against bacterial ingrowth through the nozzle orifice 5*a*, and wherein the nozzle layer 5 is deflectable to open the fluid passage 21 when the nozzle layer 5 is subjected to a differential pressure.

The valve seat 3*b* of the spray nozzle chip 1-5 may further have a valve seat intermediate layer 7*a*, the thickness of which is greater than the thickness of the intermediate layer 7, thereby forming a raised surface of the valve seat 3*b* towards which the nozzle layer 5 is internally strained, and wherein the thickness of the valve seat intermediate layer 7*a* relative to a thickness of the intermediate layer 7 defines the gap length L.

When the alternative spray nozzle chip has a bonding layer, the bonding connection between the valve seat intermediate layer 7*a* and the nozzle layer 5 initially forms a hermetic seal, which is breakable upon subjecting the nozzle layer 5 to a differential pressure for a first time.

Figure 12:
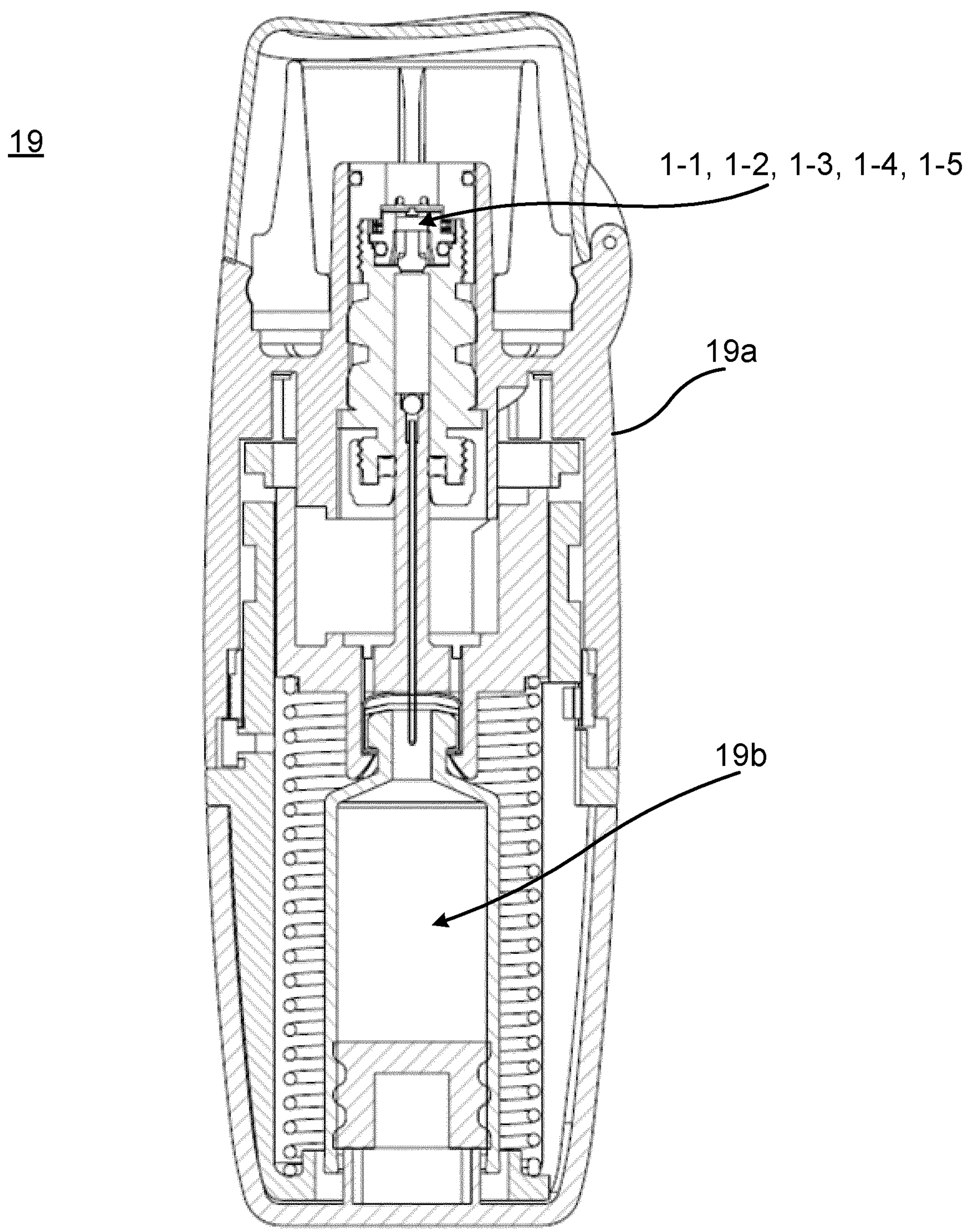
FIG. 12 is a longitudinal section of an example of a part of a medicament delivery device.

FIG. 12 shows an example of a part of a medicament delivery device 19. The medicament delivery device 19 may for example be an inhaler or an eye dispenser. The medicament delivery device 19 has a housing 19*a*, and comprises the spray nozzle chip 1-1, 1-2, 1-3, 1-4, 1-5. The medicament delivery device 19 furthermore includes a fluid container in the form of a medicament container comprising a liquid medicament. A user may initiate a spray operation for example by actuation of a button such that a liquid product in a container 19*b* is pressurised, causing the nozzle layer 5 to be subjected to a differential pressure as shown in FIG. 9, resulting in an aerosol being dispensed by the medicament delivery device 19.

The inventive concept has mainly been described above with reference to a few examples. However, as is readily appreciated by a person skilled in the art, other embodiments than the ones disclosed above are equally possible within the scope of the inventive concept, as defined by the appended claims. For example, the gap length could be set by providing a recess in the valve seat aligned with the nozzle orifice.

The invention claimed is:

1. A spray nozzle chip comprising:

a first layer provided with a first layer orifice; and a mechanically flexible nozzle layer provided with a nozzle orifice, wherein the first layer has a valve seat arranged to be aligned with the nozzle orifice, wherein the spray nozzle chip has a valve functionality obtained by movement of the nozzle layer relative to the valve seat due to pressure changes, wherein the nozzle layer is arranged at a distance from the valve seat when the nozzle layer is in a default non-pressurised state, whereby a gap with a gap length (L) is formed between the nozzle layer and the valve seat, wherein a valve seat intermediate layer is between the nozzle layer and the valve seat, wherein the first layer and the nozzle layer are connected by means of an intermediate layer, such that the valve seat intermediate layer is thicker than the intermediate layer, wherein the valve seat intermediate layer comprises a bonding layer, wherein the bonding layer is a Parylene, and wherein the bonding layer is configured to rupture when a liquid product is pressurised for a first delivery of an aerosol through the spray nozzle chip.

2. The spray nozzle chip as claimed in claim 1, wherein the thickness of the valve seat intermediate layer relative to a thickness of the intermediate layer, which connects the first layer and the nozzle layer, defines the gap length (L).

3. The spray nozzle chip as claimed in claim 1, wherein the bonding layer comprises Parylene C.

4. The spray nozzle chip as claimed in claim 1, comprising short side outer walls and long side outer walls, wherein the valve seat is arranged between the long side outer walls and the short side outer walls, wherein the nozzle layer has a width (w) defined by a distance between the long side outer walls, and wherein the nozzle layer has a nozzle layer length defined by a distance between the short side outer walls, wherein of the width (w) and the nozzle layer length, operability of the spray nozzle chip is determined only by the width (w).

5. The spray nozzle chip as claimed in claim 4, wherein the nozzle layer comprises a plurality of nozzle orifices arranged along the length of the nozzle layer.

6. The spray nozzle chip as claimed in claim 1, comprising a conformal coating provided on the first layer and on the nozzle layer.

7. A medicament delivery device comprising the spray nozzle chip as claimed in claim 1.

8. A method of manufacturing a spray nozzle chip according to claim 1, the method comprising:

a) providing a first layer which has a first layer orifice, the first layer having a valve seat, b) providing a nozzle layer which has a nozzle orifice, c) providing at least one of the first layer and the nozzle layer with an intermediate layer, and d) connecting the first layer with the nozzle layer by means of the intermediate layer.

9. The spray nozzle chip as claimed in claim 1, wherein the gap length (L) is between 0.5 nm and 300 nm to thereby seal against bacterial ingrowth through the nozzle orifice.

* * * * *